(12) United States Patent
Stengel et al.

(10) Patent No.: US 7,769,421 B1
(45) Date of Patent: Aug. 3, 2010

(54) MULTI-ELECTRODE MICRODRIVE ARRAY

(75) Inventors: Keith A. Stengel, Tucson, AZ (US);
Richard S. Olson, Tucson, AZ (US)

(73) Assignee: Neuralynx, Inc., Bozeman, MT (US)

( * ) Notice: Subject to any disclaimer, the term of this patent is extended or adjusted under 35 U.S.C. 154(b) by 1052 days.

(21) Appl. No.: 11/457,407

(22) Filed: Jul. 13, 2006

Related U.S. Application Data

(60) Provisional application No. 60/698,755, filed on Jul. 13, 2005.

(51) Int. Cl.
*A61B 5/0478* (2006.01)

(52) U.S. Cl. ...................... 600/378; 606/129

(58) Field of Classification Search ................. 600/378; 606/129
See application file for complete search history.

(56) References Cited

U.S. PATENT DOCUMENTS

| | | | | |
|---|---|---|---|---|
| 3,089,483 A | * | 5/1963 | Sheatz .................... 600/377 |
| 4,245,645 A | * | 1/1981 | Arseneault et al. .......... 600/378 |
| 5,928,143 A | | 7/1999 | McNaughton ............ 600/373 |
| 6,249,691 B1 | * | 6/2001 | Pezaris et al. .............. 600/378 |
| 7,493,178 B2 | * | 2/2009 | Abu Nassar et al. ......... 700/56 |
| 7,551,951 B1 | * | 6/2009 | Osorio et al. .............. 600/378 |

* cited by examiner

Primary Examiner—Lee S Cohen
(74) Attorney, Agent, or Firm—Hayes Soloway P.C.

(57) ABSTRACT

An apparatus for use in neurophysiological research and clinical diagnosis comprises a hollow body having a plurality of electrode wires slidably carried therein. Each electrode wire is carried on a shuttle that is slidably mounted in a slot in an interior wall of the hollow body.

19 Claims, 16 Drawing Sheets

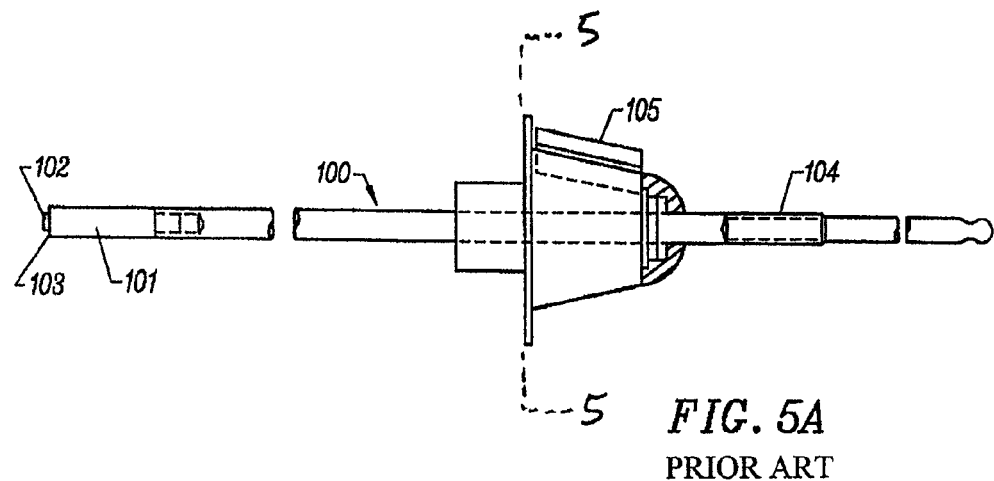
FIG. 5A
PRIOR ART
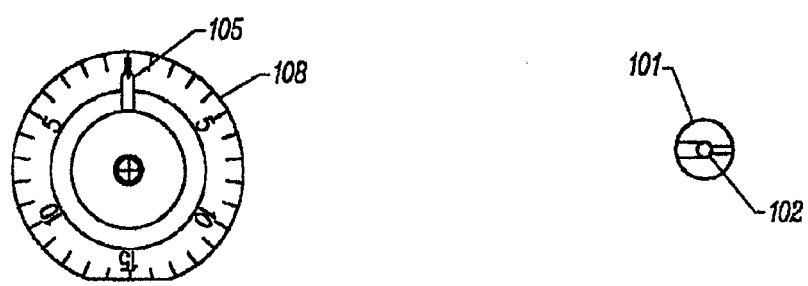
FIG. 5B
PRIOR ART
FIG. 5C
PRIOR ART

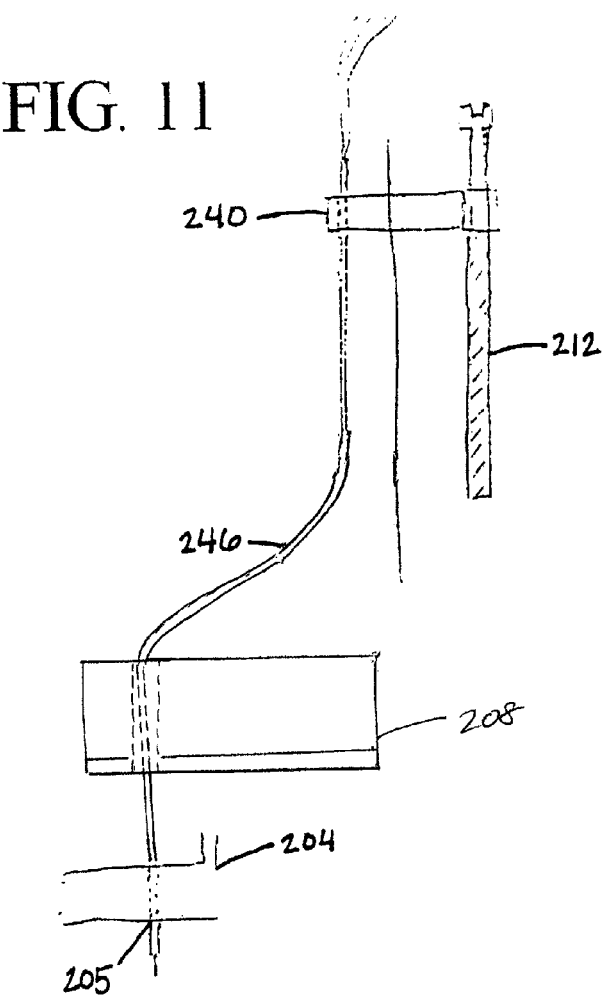
FIG. 11
FIG. 12
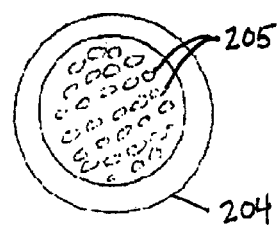
FIG. 13
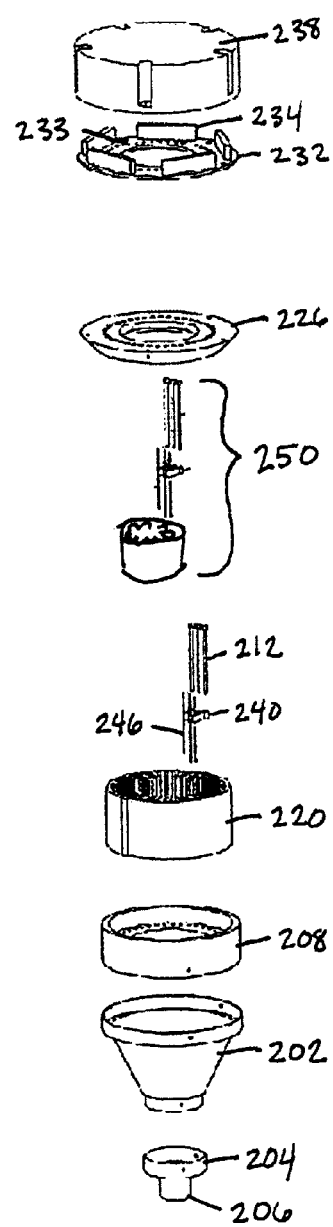

MULTI-ELECTRODE MICRODRIVE ARRAY

CROSS-REFERENCE TO RELATED APPLICATION

This application claims benefit of U.S. Provisional Ser. No. 60/698,755 filed Jul. 13, 2005.

FIELD OF THE INVENTION

This invention relates generally to multi-electrode microdrive arrays. The invention has particular utility in connection with implantable micro-electrode microdrive arrays for use with brain research instruments, and will be described in connection with such utility, although other utilities are contemplated.

BACKGROUND OF THE INVENTION

Implantable independently adjustable electrodes are used for in vivo and in vitro neurophysiological research. Prior art brain research instrumentation includes movable single channel or single electrode mechanisms which were limited to recording from single locations in the brain. Early research tended to be concentrated in sensory portions of the brain such as the visual cortex. For example, the research would seek to identify what particular stimulus in the subject's visual field would cause an individual neuron in the visual cortex to fire. The prior art single electrode mechanisms were capable of being moved to different locations in the brain but were only capable of recording from a single neuron or a small neuron cluster at a time.

The prior art also includes apparatus with multiple electrodes whose position in space is fixed relative to the other electrodes. These prior art electrodes are capable of recording timing or firing patterns of multiple neurons or multiple small clusters of neurons. The importance of being able to record timing patterns is critical to understanding higher order functions of the brain. However, the multi-channel or multi-electrode prior art devices could only be used in restrained animal subjects and were not capable of being moved within the brain. Thus, the timing patterns that could be recorded within the brain were limited by the number of electrodes and to only those patterns that occurred between the individual neurons or small neuron clusters that happen to be near the tips of the recording electrodes. Another disadvantage of the fixed array of electrodes is that the research is inherently limited to those brain functions performed by a non-moving subject.

The foregoing discussion of the prior art derives largely from U.S. Pat. No. 5,928,143 (the '143 patent) in which there is described an implantable multi-electrode microdrive array that may be made sufficiently small and light weight and it may be implanted on animals as small as rats. Referring to FIGS. 1-3, the multi-electrode microdrive array made in accordance with the '143 U.S. patent comprises an array of elongated guide cannulae referred to generally as 20 which provide a guide means for the recording electrodes. In the embodiment shown the total number of guide cannulae provided is 14. The 14 cannulae and their associated drive mechanisms are identical. Each of the guide cannulae, such as individual cannula 21 shown in FIG. 1, has an upper end 21a and a lower end 21b. The lower ends of each cannula are aligned parallel with and are adjacent each other. The 14 guide cannulae, shown in the embodiments of FIGS. 1 and 2, easily fit into a passageway 8 formed in the skull 9 of the subject animal.

The upper end 21a of cannula 21 is inclined outwardly from the central vertical axis A of the apparatus 10 by preferably an angle of 30°. Other angles may be used. By inclining the upper ends of the array of cannulae 20 outwardly, as shown best in FIG. 2, sufficient spacing is obtained between adjacent cannulae that electrodes carried within the cannulae are capable of being independently adjusted relative to one another.

A support means 40 is provided for the array of guide cannulae 20. The support means is preferably a mechanical plastic core. The plastic core has an upper end 42 and a lower end 43. A first passageway 44 is formed in the lower end 43 of the plastic core, and is adapted to receive a cylindrical bushing 49 with an internal passageway 48 through which the lower ends of the array of guide cannulae 20 extend, as shown in FIG. 3. The support means or plastic core 40 also has a plurality of inclined passageways such as 46 formed in its upper portion 42 for each upper portion of each guide cannula. Each of the inclined passageways such as 46 communicates with the passageway 48 formed by bushing 49 and extends upwardly and preferably outwardly at an angle of 30° of the vertical axis A. Each of the guide cannulae remains fixed relative to support means 40 with upper end 21a terminating just below the upper surface 42a of support means 40.

Each of said guide cannulae in the array 20 carries one or more electrodes. For example, guide cannula 21 shown in FIG. 1 carries in the preferred embodiment a group of four electrodes 51, which is referred herein as a tetrode. The tetrode 51 has an upper end 51a which is located in the upper portion 21a of guide cannula 21. The tetrode 51 has a lower portion 51b which is capable of being moved downwardly into the brain 7 to various depths.

According to the '143 patent, the preferred electrode assembly includes a tetrode which comprises four recording probes made by twisting together four strands of polyamide-coated, 14 micron diameter, nichrome wires. To obtain adherence and stiffness, the insulation is briefly softened by heating, while the wires are under tension, and then allowed to cool. Wires are cut flat at the same level and each tip is gold-plated separately to reduce the impedance of individual electrodes to 400-500 K-ohm. The overall diameter of each tetrode is approximately 40 microns. The tetrode is mounted and glued into two nested polyamide tubes, those tubes being 78 and 110 microns outside diameter, respectively, which are then mounted in the support means 40. The smaller tubing (78 micron O.D.) forms each guide cannula 21 and the larger tubing (110 micron O.D.) forms each drive cannula 71.

Electrode adjustment means shown generally as 70 (FIG. 1) are connected to the upper end of each electrode and each guide cannula. The electrode adjustment drive means 70 is capable of moving the electrode or electrode bundle in each guide cannula independently of the electrodes carried in the other guide cannulae in the array 20. As shown in FIG. 1, each electrode adjustment means 70 is capable of moving between the position shown in solid lines downwardly to the position shown in phantom as 70a. Electrode adjustment means 70 in the preferred embodiment shown in FIG. 1 includes a drive cannula 71 slidably mounted over the upper end 21a of guide cannula 21, electrode drive means 75, adjustment rod 72 and guide rod 85 described below. Each guide cannula 21 (typically 78 micron O.D.) slidably nests in drive cannula 71 (typically 110 micron O.D.). The top of electrode 51a slides through and is attached to the top of drive cannula 71 by glue. A plurality of adjustment rod means 72 (FIG. 3) are provided, each of which is carried by support means 40 and each of which is mounted parallel to its respective guide cannula 21.

Adjustment rod means 72 is preferably an 0.080" headless stainless screw, threaded into support means 40.

Referring also to FIGS. 4a and 4b, an electrode drive means 75 is carried by each adjustment rod 72 as shown best in FIG. 3. Electrode drive means 75 includes a cylindrically shaped nut 76 with a threaded inner bore 77 which threads onto threaded rod 72. Nut 76 has a turning slot 78 formed in its upper surface.

Nut 76 is connected to a generally triangular shaped bridge 80. Bridge 80 has a first bore 81 formed therein for carrying drive cannula 71. Nut 76 has an upper flange 76a and a lower flange 76b which cause bridge 80 to move upwardly and downwardly on rod 72 as the nut 76 is turned. Bridge 80 has a second bore 82 formed therein for receiving a guide rod 85 (FIG. 2). Guide rod 85 prevents rotation of bridge 80 relative to adjustment rod 72 as nut 76 is rotated. Guide rod 85 is parallel to adjustment rod 72 and is cemented into support means 40.

Referring also to FIGS. 5a-5c, an electrode adjustment tool 100 is provided having a hollow drive sleeve 101 adapted to slide over the top of adjustment rod 72 (FIG. 3). A drive tip 102 is formed at the distal end 103 of sleeve 101. Drive tip 102 engages turning slot 78. A turning knob 105 is carried near the proximal end 104 of sleeve 101 and carries a scale 108 to indicate the motion imparted to an electrode. Rotation of knob 105 imparts axial motion to drive cannula 71 and to the electrode or electrodes 51 carried within that drive cannula.

While the multi-electrode microdrive array described in the aforesaid '143 patent provides significant improvements over prior art devices in providing an increased number of independently adjustable recording electrodes in an array that is small enough and light weight enough to be easily carried on the skull of the subject animal, while providing free motion of the subject, the multi-electrode microdrive array of the '143 patent is expensive to manufacture requiring painstaking and time consuming machining and assembly. The multi-electrode microdrive array of the '143 patent also is difficult to use in the field requiring painstaking and time consuming manipulation to adjust individual electrodes into position.

BRIEF DESCRIPTION OF THE INVENTION

The present invention overcomes the aforesaid and other disadvantages of prior art multi-electrode microdrive arrays including multi-electrode microdrive arrays made in accordance with the '143 patent by providing a multi-electrode microdrive array in which electrode wires are supported by shuttles which in turn are slidably mounted in slots formed in a support. In a preferred embodiment of the invention, the electrode wires are carried within capillary tubing.

BRIEF DESCRIPTION OF THE DRAWINGS

Further features and advantages of the present invention will be seen from the following detailed description, taken in connection with the accompanying drawings, wherein like numerals depict like parts, and wherein:

FIG. 5a is a side elevational view of a prior art electrode adjustment tool for the apparatus of FIG. 1;

FIG. 5b is a section on the line 5-5 of FIG. 5a;

FIG. 5c is a top end view of the tip of the adjustment tool of FIG. 5a;

FIG. 11 is a side elevational view showing portions of the shuttle and guide part of the apparatus of the present invention;

FIG. 12 is a bottom plan view of a portion of the apparatus of the present invention; and FIG. 13 is a view similar to FIG. 6a of an alternative multi-electrode microdrive array apparatus made in accordance with the present invention.

DETAILED DESCRIPTION OF THE INVENTION

Figure 10A:
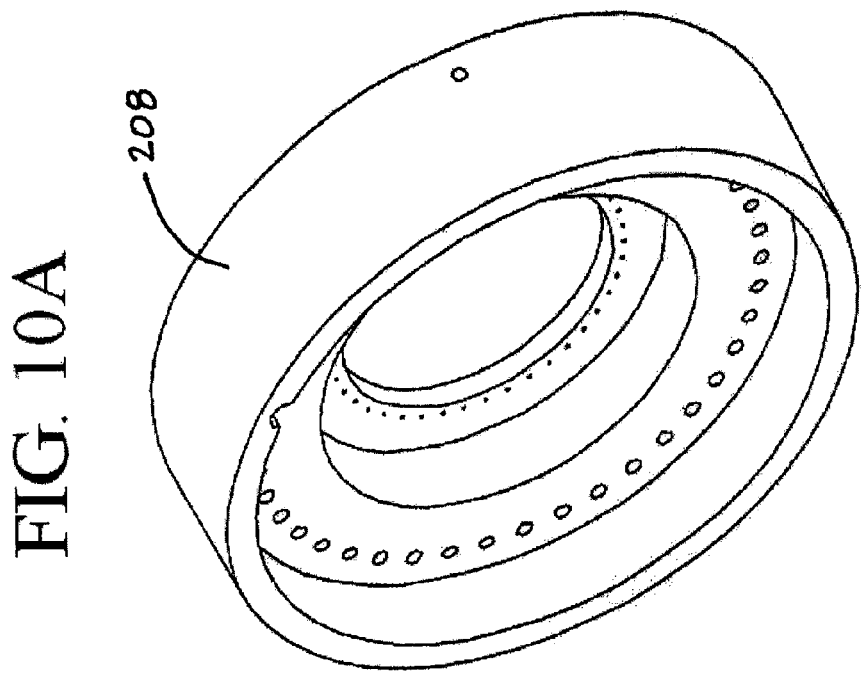
FIG. 10 is a top plan view and FIG. 10a is a perspective view of a bottom guide ring part of the apparatus of FIG. 6.
Figure 10:
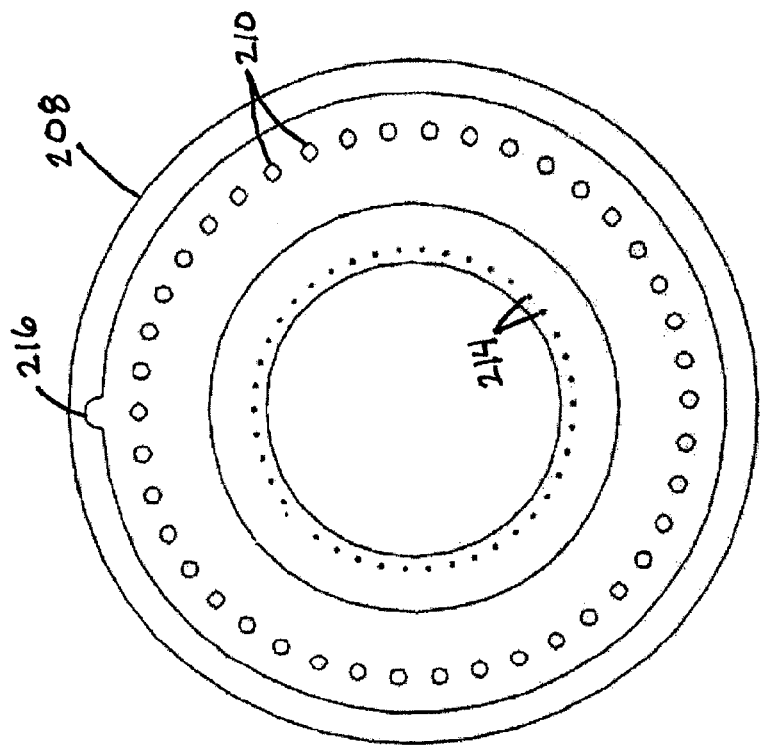
Figure 14:
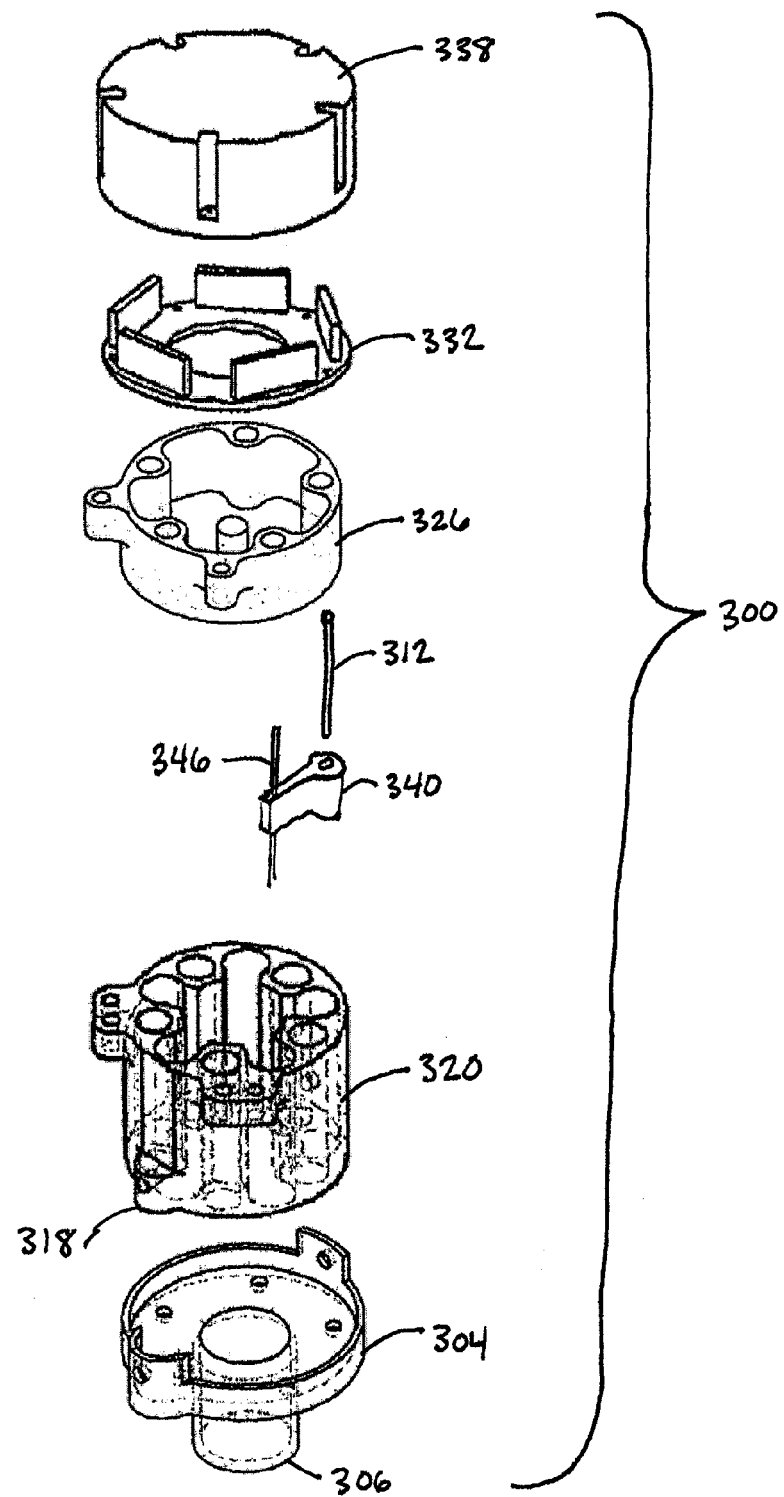
FIG. 14 is an exploded view of a multi-electrode microdrive array apparatus according to yet another embodiment of the present invention.
Figure 15A:
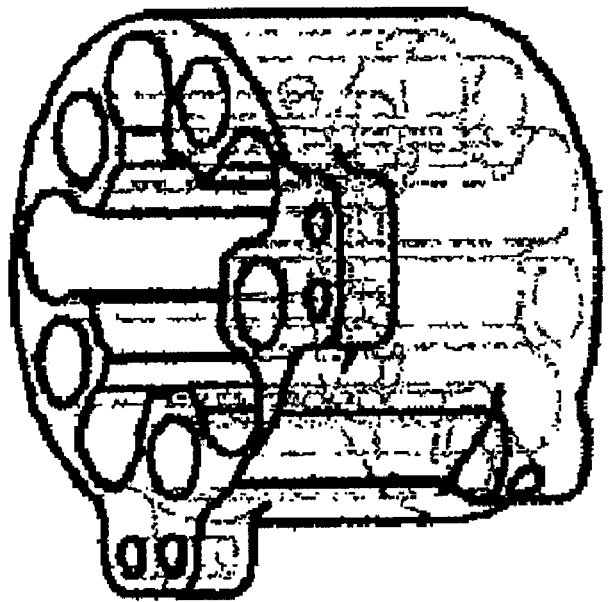
FIG. 15 is a top plan view and FIG. 15a is a perspective view of a drive body part of the apparatus of FIG. 14.
Figure 15:
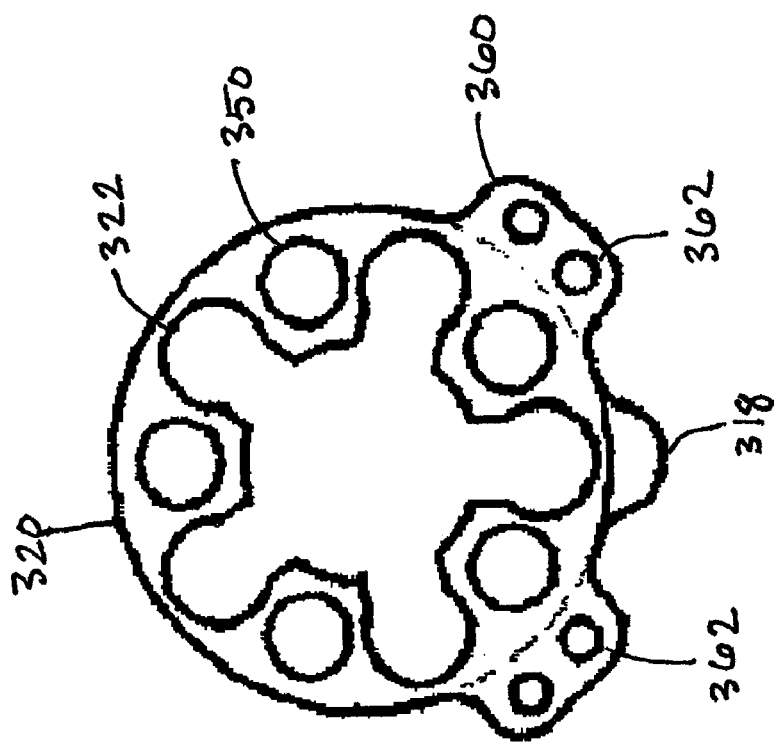
Figure 16A:
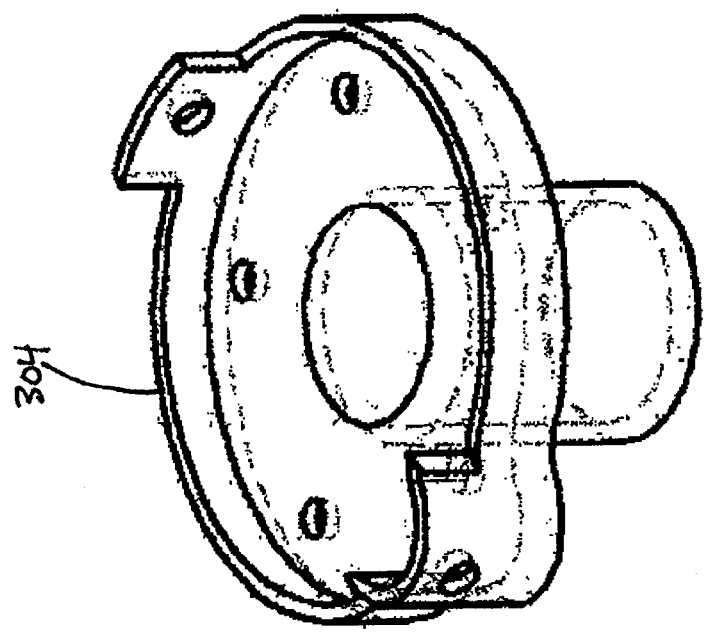
FIG. 16 is a top plan view and FIG. 16a is a perspective view of a drive tip part of the apparatus of FIG. 14.
Figure 16:
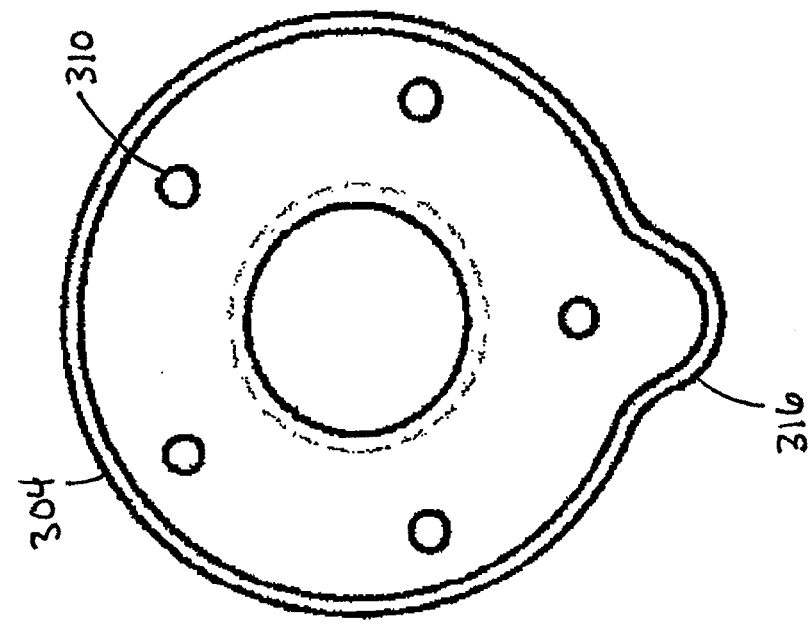
Figure 17A:
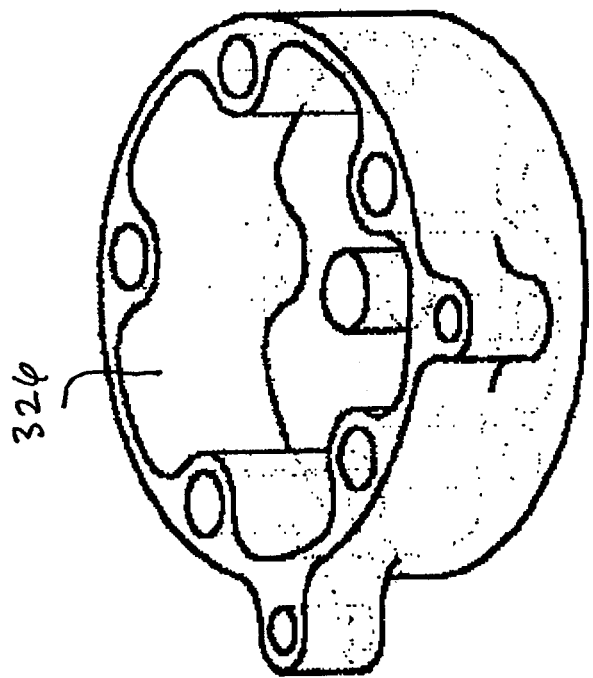
FIG. 17 is a top plan view and FIG. 17a is a perspective view of an inner drive cap part of the apparatus of FIG. 14.
Figure 17:
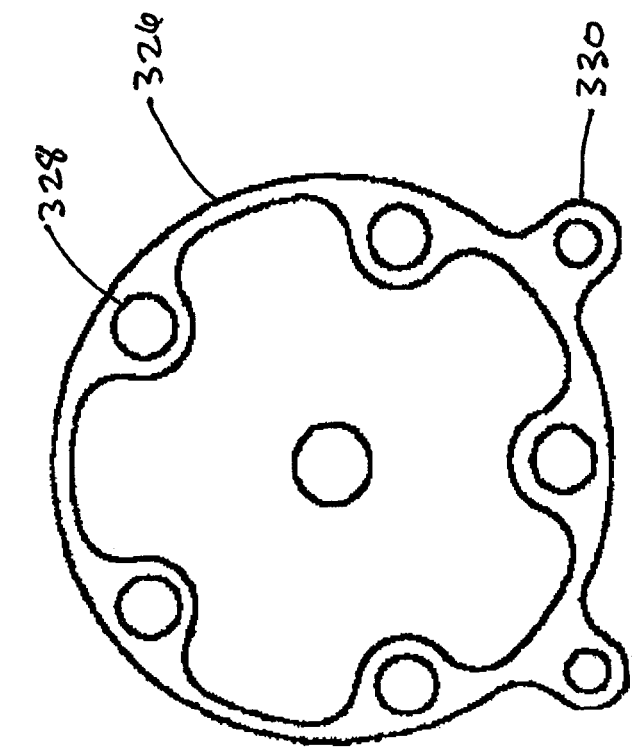

Referring to FIGS. 6-10 a multi-electrode microdrive array apparatus 200 made in accordance with the present invention comprises a two piece lower shroud or casing 202, 204. Shroud 204 is stepped down at its distal end 206 and sized to easily fit within a passageway (not shown) formed in the skull in a subject animal. Referring also to FIGS. 10 and 10a, a lower guide ring 208 is mounted to the top of shroud 202. Lower guide ring 208 includes a plurality of through holes 210 for accommodating the distal ends of adjustment screws 212 and a second plurality of holes 214 which act as guides for individual electrodes or electrode assemblies as will be described in detail hereinafter. An alignment channel 216 is formed in a wall of the lower guide ring 208 for accommodating a boss 218 formed in an outer wall of main body 220.

Body 220 is cylindrical in shape, and includes a plurality of key hole shaped slots 222 for accommodating shuttles 240 and adjustment screws 212 as will be described in detail hereinafter. A top guide ring 226 is fitted over the top of body 220 and includes a plurality of adjustment screw holes 228. Top guide ring 226 also includes a channel 230 for accommodating boss 218. As will be appreciated, channels 216 and 230 and boss 218 ensure precise alignment of guide ring 208, body 220 and top guide ring 226. Thus, holes 210 and 228 will be precisely aligned over one another, and aligned with the rounded heads of slots 222. A circuit board support ring 232 is mounted above top guide ring 226, and carries a plurality of circuit boards 234. Circuit board support ring 232 also includes a plurality of adjustment screw holes 233 which are aligned with holes 228 and holes 214. Circuit board support ring 232 is aligned with top guide ring by driving screws (not shown) through holes 235 and 227 pre-formed in the circuit board support ring 232 and top guide ring 226, respectively.

A removable cover 238 completes the outer casing.

Figure 1:
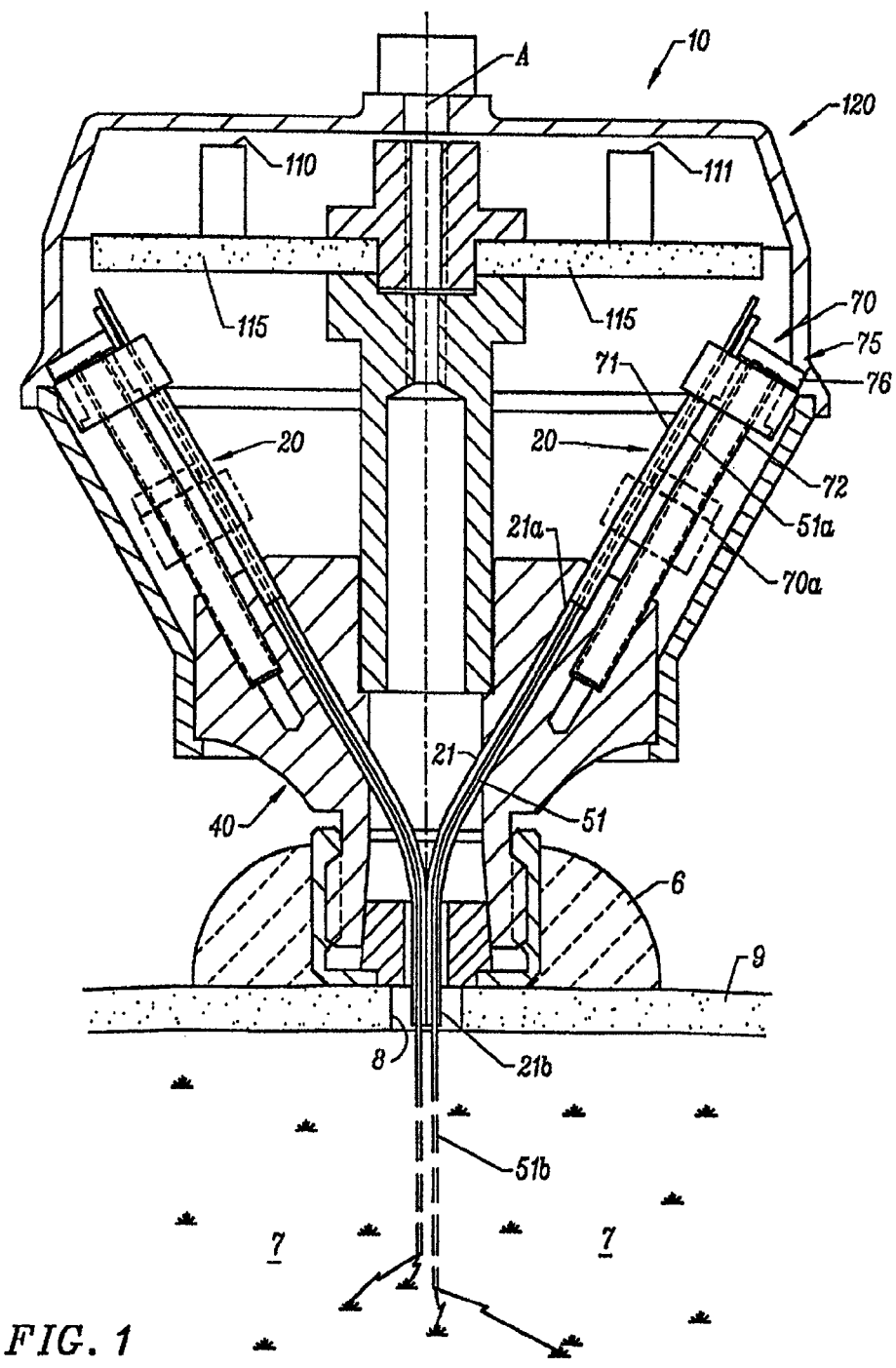
FIG. 1 is a sectional view of apparatus made in accordance with the prior art shown schematically as attached to the skull of a laboratory animal.
Figure 2:
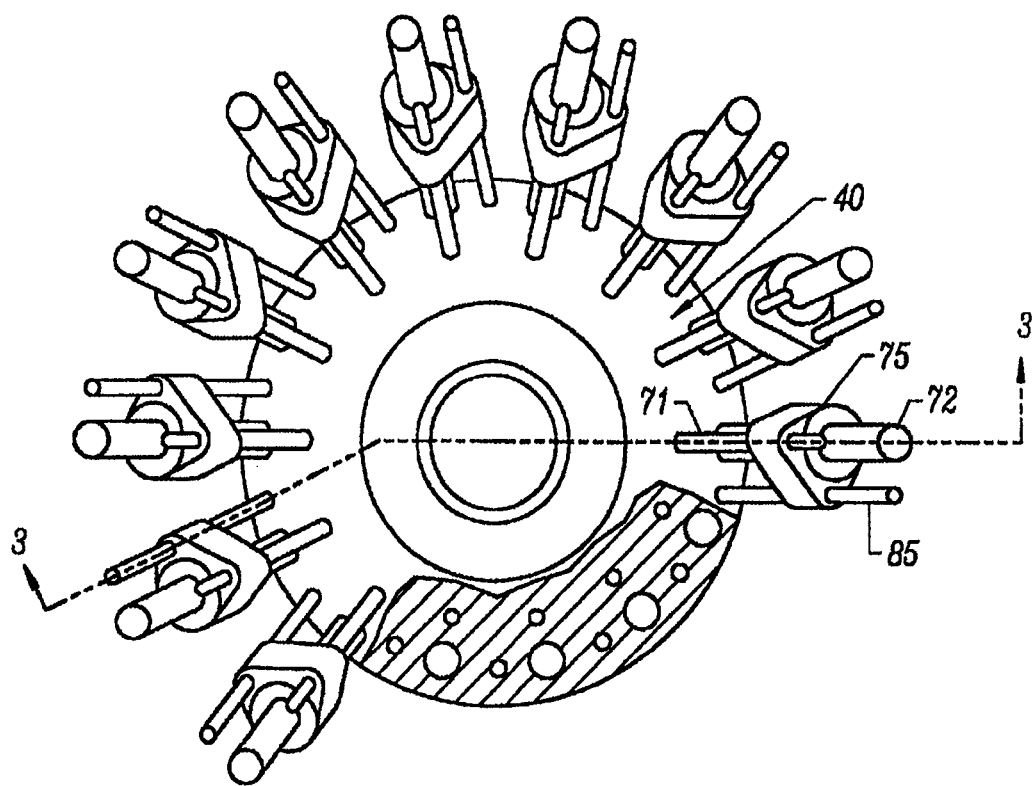
FIG. 2 is a top perspective view of the apparatus of claim 1, and shows how the electrode adjustment mechanisms are mounted relative to each other.
Figure 3:
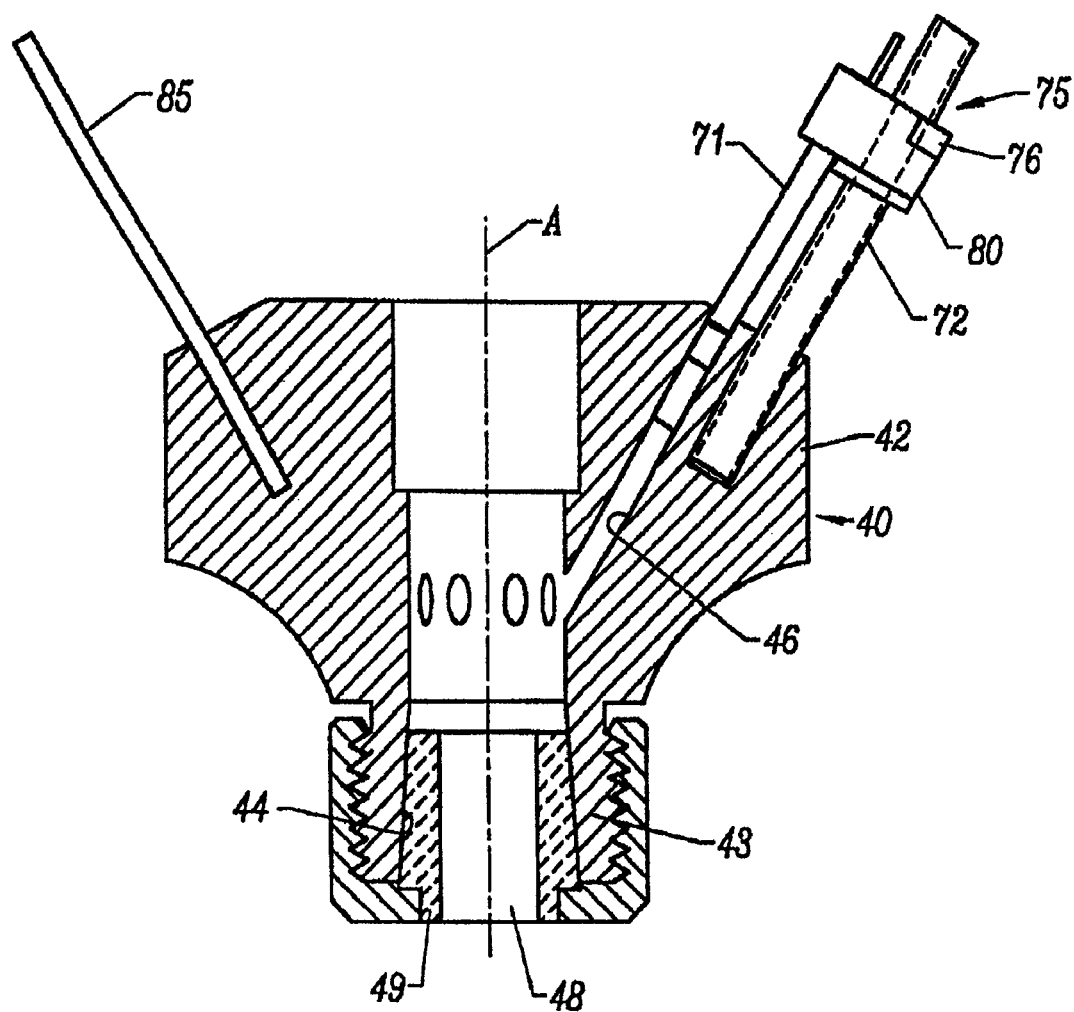
FIG. 3 is a sectional view on the line 3-3 of FIG. 2.
Figure 4A:
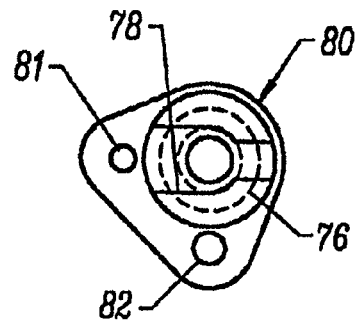
FIGS. 4a and 4b are a top and side elevational view, respectively, of the electrode adjustment mechanism of the apparatus of FIG. 1.
Figure 4B:
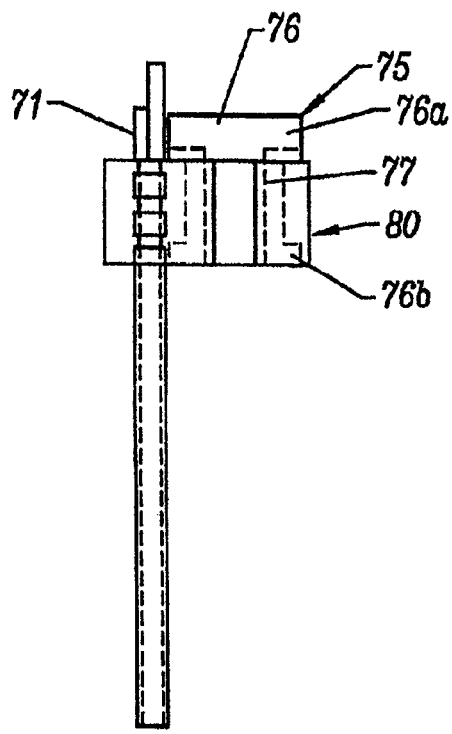
Figure 6:
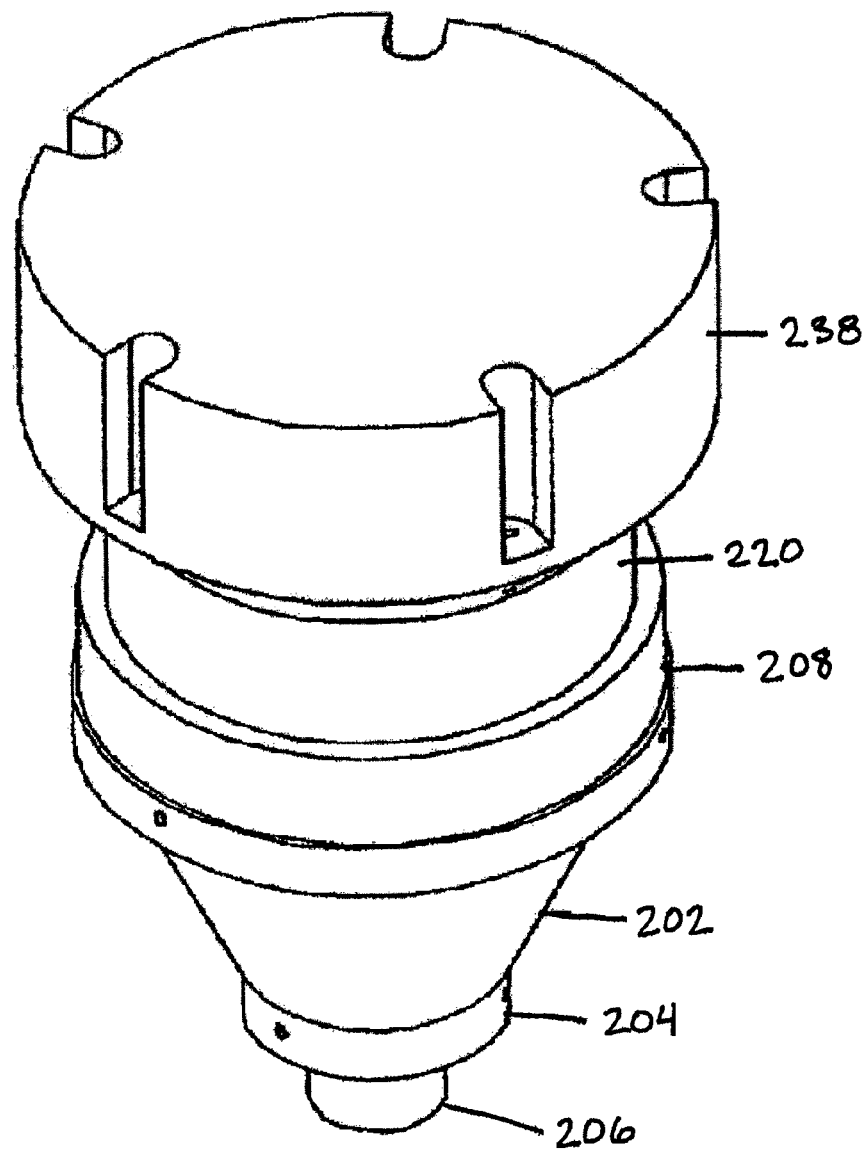
FIG. 6 is a perspective view and FIG. 6a an exploded view of a multi-electrode microdrive array apparatus made in accordance with a preferred embodiment of the present invention.
Figure 6A:
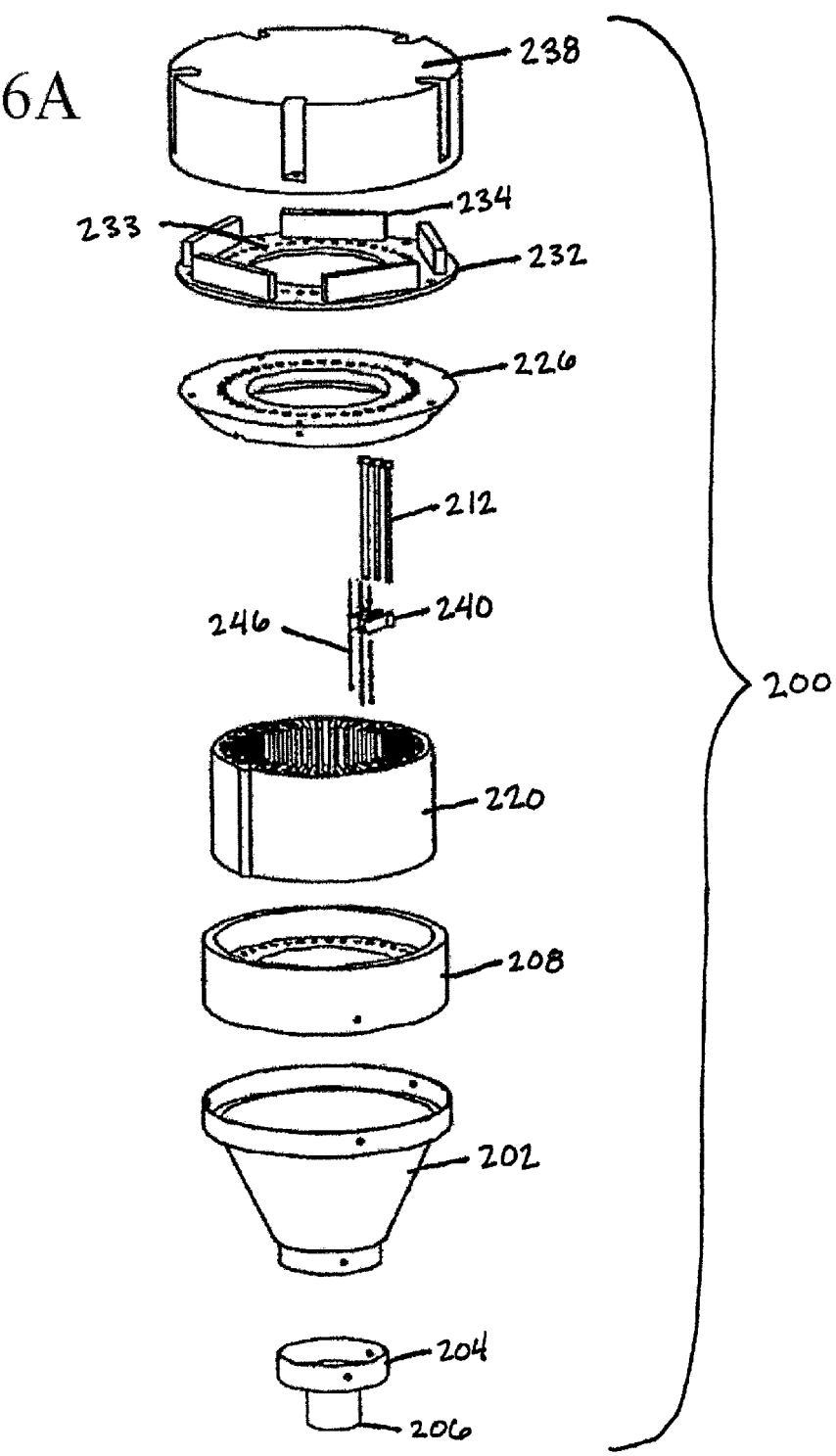
Figure 7A:
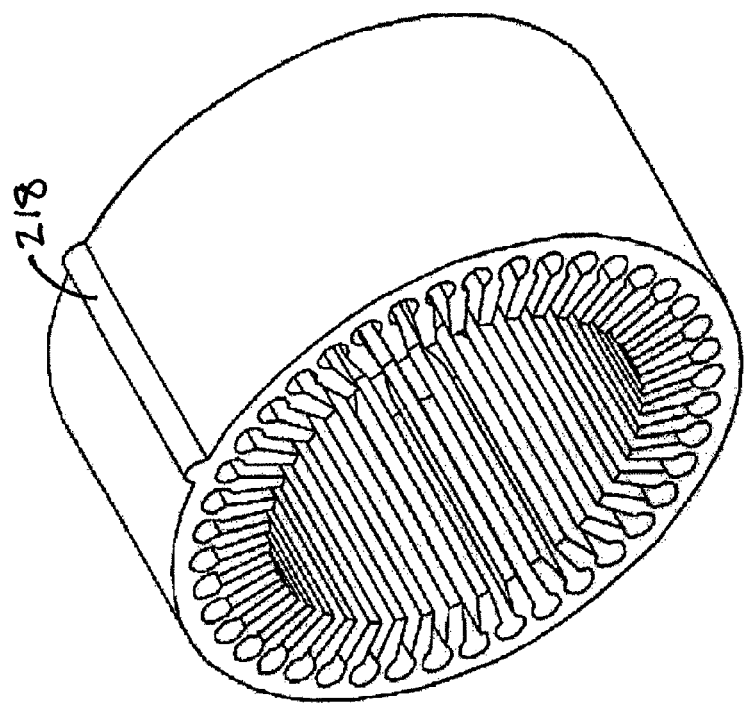
FIG. 7 is a top plan view and FIG. 7a a perspective view of the main body portion of the apparatus of FIG. 6.
Figure 7:
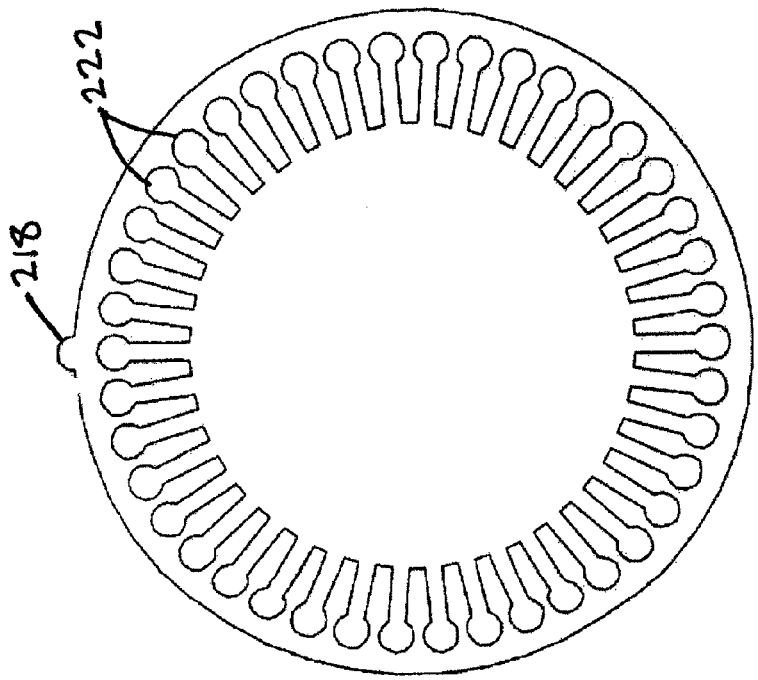
Figure 8A:
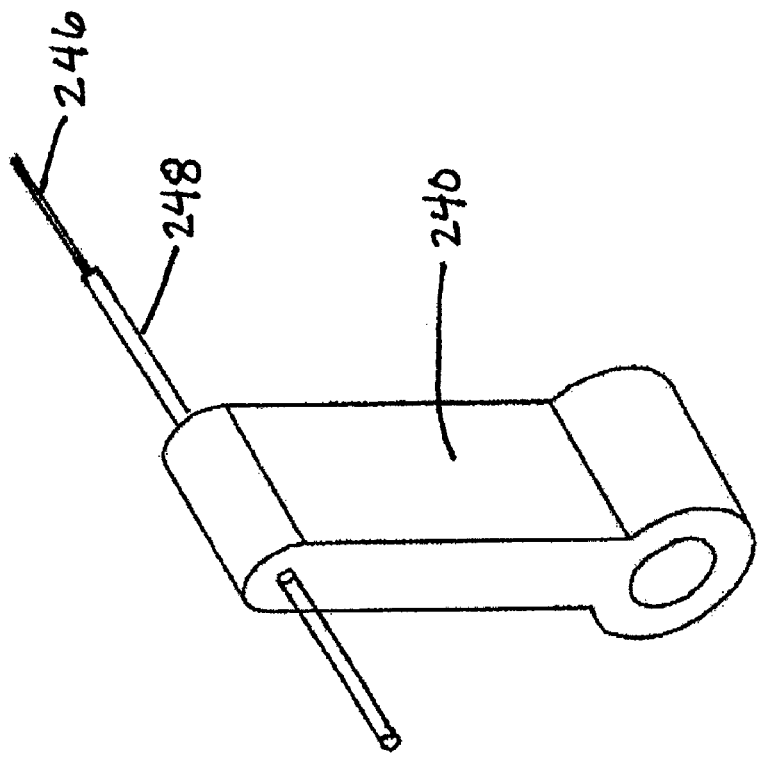
FIG. 8 is a top plan view and FIG. 8a a perspective view of a shuttle part of the apparatus of FIG. 6.
Figure 8:
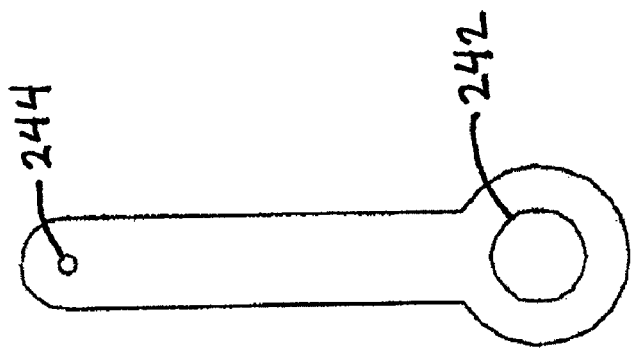
Figure 9A:
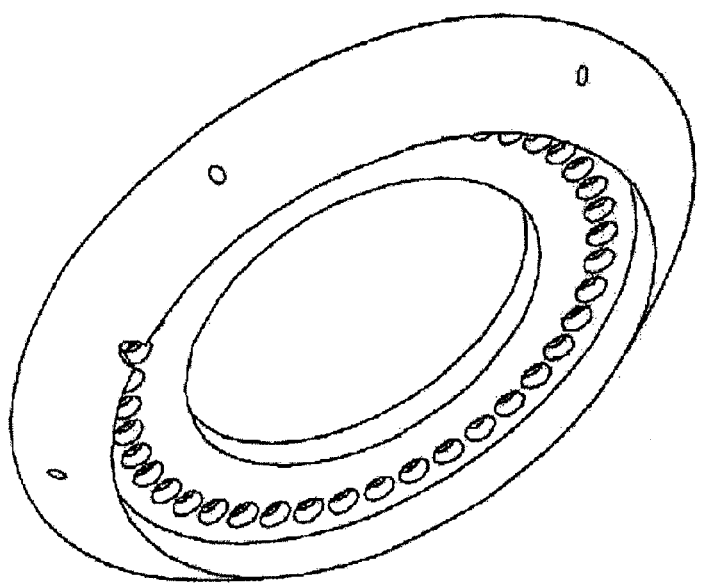
FIG. 9 is a top plan view and FIG. 9a is a perspective view of a top guide ring part of the apparatus of FIG. 6.
Figure 9:
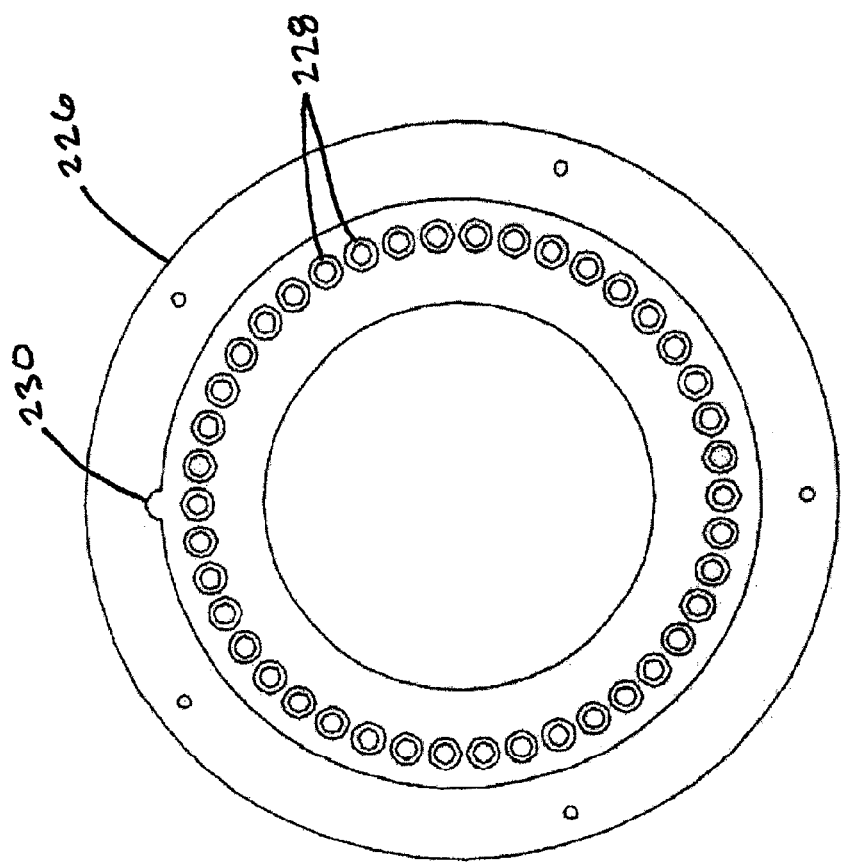

Referring in particular to FIGS. 8 and 8a, a key shaped shuttle 240 is slidably mounted in slot 222, one shuttle per slot. Slots 222 may be formed by milling or may be molded in. Each shuttle includes a through threaded through-hole 242 sized to accommodate an adjustment screw 212, and a second through hole 244 sized to accommodate a wire electrode 246. In a preferred embodiment of the invention, each wire electrode 246 is threaded through a capillary tubing 248 having an OD just slightly smaller than the ID of hole 244 so that the capillary can be threaded into hole 244 and held in position by friction. In a preferred embodiment of the invention, the capillary tubing comprises fused silica tubing available from Poly Micro Technologies, LLC of Phoenix, Ariz.

In use, the multi-electrode microdrive array is mounted to the skull of a test animal, and shuttles 240 carrying capillary tubing and electrodes 246 are pushed through holes 205 formed through the bottom wall of shroud 204 as will be discussed below, and advanced so that their distal ends are located in a desired position by adjusting screws 212.

A feature and advantage of the present invention over the prior art multi-electrode drive array apparatus results from the use of capillary tubing surrounding the electrodes. The capillary tubing exhibits a combination of stiffness, flexibility and lack of bending memory to allow a free-form, unsupported consistent movement of the electrode from the shuttle, through holes 205 formed through the bottom wall of shroud 204, and permits off-axis driving of unsupported capillary tubing without complicated mechanical guides (see FIG. 11). This in turn allows the electrode exit pattern to be independently placed (user defined). This also permits tight electrode spacing (see FIG. 12).

Another feature and advantage of the present invention over prior art multi-electrode microdrive array apparatus such as described in the '143 U.S. patent is the significantly reduced number of parts as compared to the '143 patented apparatus. As a result, manufacturing and assembly costs are substantially reduced. Also, the reduced number of parts permits a greater number of electrodes to be packed into a base.

The invention is susceptible to modification. For example, while a single circle of shuttles is shown, it is possible to load a second, smaller diameter multi-electrode microdrive array shown generally at 250 in the central hollow space 252. This is illustrated in FIG. 13.

Another embodiment of the invention is shown in FIGS. 14-17. This embodiment is similar in function but is smaller and has mass and fewer parts. In this configuration, the invention will be cheaper to manufacture and less of a nuisance to the subject animal.

According to this latter embodiment, the lower shroud or casing and the lower guide ring of the previously described embodiments have been combined into a single part as the drive tip 304. The drive tip 304 contains a distalmost end 306, sized to fit into a passageway created in the skull of the subject animal; an alignment guide 316 used to align the drive body 320; and a plurality of holes to accept the distal end of adjustment screws 312. The adjustment screws 312 operate in the same manner as the adjustment screws 212 in the above described embodiments.

The drive body 320 of this latter embodiment functions identical to the main body 220 of the above described embodiments except for the fact that drive body 320 is smaller and contains fewer keyhole shaped slots 322. The shuttles 340 operate in the same manner as the shuttles 240 in the above discussed embodiments. A lower alignment boss 318 aligns with the alignment channel 316 of the drive tip 304 such that the holes 310 are perfectly aligned with the center of the keyhole shaped slots 322. The drive body 320 also contains a number of holes 350 that are present to reduce the amount of material in the drive body, consequently reducing weight of the apparatus.

Two upper alignment bosses 360 protrude horizontally from the upper end of the drive body 320. These upper alignment bosses 360 of the drive body 320 contain two sets of holes used to align the inner drive cap 332 and the end cap 338. The inner set of holes 362 of the upper alignment bosses align with holes in two alignment bosses of an inner drive cap 330. These are aligned such that holes 328 in the inner drive cap 330 align with the slots 322 of the drive body 320 and the holes 310 of the drive tip 304. A circuit board ring 332 attaches to the top of the inner drive cap 330. Finally, a removable cover 338 is provided.

Still other changes may be made without departing from the spirit and scope of the invention.

The invention claimed is:

1. An apparatus for use in neurophysiological research and clinical diagnosis comprising:
   a hollow body having a plurality of electrode wires slidably carried therein, wherein each electrode wire is carried on a shuttle that is slidably mounted in a slot in an interior wall of said body; and
   a second hollow body having a plurality of electrode wires carried therein, located within the hollow of the first body.

2. The apparatus of claim 1, wherein the electrode wires carried in the second body are carried on shuttles that are slidably mounted in slots in an interior wall of said second body.

3. The apparatus of claim 2, wherein the slots are key hole-shaped in plan.

4. The apparatus of claim 1, wherein the electrode wires are carried within a sheath.

5. The apparatus of claim 4, wherein the sheath comprises capillary tubing.

6. An apparatus for use in neurophysiological research and clinical diagnosis comprising:
   a first cylindrical hollow body having a plurality of electrode wires slidably carried therein, and further having a plurality of slots arranged in a circular pattern around an interior wall of said first body, wherein each electrode wire is carried on a shuttle that is slidably mounted in one of said slots, and a second hollow body having a plurality of electrode wires carried therein, located within the hollow of the first body.

7. The apparatus of claim 6, and further comprising an adjustment device for moving the electrode wires independently of one another.

8. The apparatus of claim 7, wherein the adjustment device comprises a threaded screw.

9. The apparatus of claim 6, wherein the slots are key hole-shaped in plan.

10. The apparatus of claim 6, wherein the electrode wires are carried within a sheath.

11. The apparatus of claim 10, wherein the sheath comprises capillary tubing.

12. The apparatus of claim 6, wherein the electrode wires carried in the second body are carried on shuttles that are slidably mounted in slots in an interior wall of said second body.

13. The apparatus of claim 12, wherein the slots in the second body are key hole-shaped in plan.

14. An apparatus for use in neurophysiological research and clinical diagnosis comprising:
   an upper guide ring having a plurality of holes for an adjustment device;
   a hollow body having a plurality of electrode wires slidably carried therein, and further having a plurality of slots arranged around an interior wall of said body, wherein each electrode wire is carried on a shuttle that is slidably mounted in one of said slots; and
   a lower guide ring having a plurality of holes for an adjustment device, wherein the plurality of holes of the upper guide ring, the plurality of slots of the hollow body, and the plurality of holes of the lower guide ring are aligned with one another.

15. The apparatus of claim 14, and further comprising an adjustment device for moving the electrode wires independently of one another.

16. The apparatus of claim 15, wherein the adjustment device comprises a threaded screw.

17. The apparatus of claim 14, wherein the slots are key hole-shaped in plan.

18. The apparatus of claim 14, wherein the electrode wires are carried within a sheath.

19. The apparatus of claim 18, wherein the sheath comprises capillary tubing.

* * * * *